(12) United States Patent
Rezach

(10) Patent No.: US 8,246,658 B2
(45) Date of Patent: Aug. 21, 2012

(54) SPINAL CONNECTOR ASSEMBLY

(75) Inventor: William Alan Rezach, Atoka, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 120 days.

(21) Appl. No.: 12/915,766

(22) Filed: Oct. 29, 2010

(65) Prior Publication Data

US 2012/0109209 A1 May 3, 2012

(51) Int. Cl.
*A61B 17/70* (2006.01)
(52) U.S. Cl. ............................................. 606/264
(58) Field of Classification Search ............. 606/54–60, 606/246, 250–279, 300–331; 403/21–22
See application file for complete search history.

(56) References Cited

U.S. PATENT DOCUMENTS

| | | | |
|---|---|---|---|
| 5,047,029 A * | 9/1991 | Aebi et al. ................. 606/264 |
| 5,053,034 A * | 10/1991 | Olerud ........................ 606/246 |
| 5,741,255 A * | 4/1998 | Krag et al. .................. 606/264 |
| 5,928,232 A * | 7/1999 | Howland et al. ........... 606/276 |
| 6,210,413 B1 * | 4/2001 | Justis et al. ................. 606/254 |
| 6,231,575 B1 * | 5/2001 | Krag ............................ 606/264 |
| 6,478,798 B1 * | 11/2002 | Howland ..................... 606/264 |
| 6,520,962 B1 * | 2/2003 | Taylor et al. ............... 606/278 |
| 6,524,315 B1 * | 2/2003 | Selvitelli et al. ............. 606/70 |
| 6,575,658 B2 * | 6/2003 | Daniel et al. ............... 403/316 |
| 6,673,074 B2 * | 1/2004 | Shluzas ....................... 606/278 |
| 6,685,705 B1 * | 2/2004 | Taylor ......................... 606/278 |
| 6,832,999 B2 * | 12/2004 | Ueyama et al. ............ 606/264 |
| 6,872,209 B2 * | 3/2005 | Morrison .................... 606/278 |
| RE39,035 E * | 3/2006 | Finn et al. ................... 606/264 |
| 7,575,587 B2 * | 8/2009 | Rezach et al. .............. 606/278 |
| 7,651,516 B2 * | 1/2010 | Petit et al. ................... 606/279 |
| 7,753,940 B2 * | 7/2010 | Veldman et al. ........... 606/278 |
| 7,850,715 B2 * | 12/2010 | Banouskou et al. ....... 606/246 |
| 7,896,905 B2 * | 3/2011 | Lee et al. .................... 606/271 |
| 8,021,398 B2 * | 9/2011 | Sweeney et al. ........... 606/269 |
| 8,066,746 B2 * | 11/2011 | Glerum et al. ............. 606/278 |
| 8,070,781 B2 * | 12/2011 | Harper ........................ 606/264 |
| 8,137,386 B2 * | 3/2012 | Jackson ...................... 606/266 |
| 2002/0173789 A1 * | 11/2002 | Howland ....................... 606/61 |
| 2003/0176862 A1 * | 9/2003 | Taylor et al. .................. 606/61 |
| 2003/0191473 A1 * | 10/2003 | Taylor ........................... 606/61 |
| 2004/0010253 A1 * | 1/2004 | Morrison ...................... 606/61 |
| 2004/0059331 A1 * | 3/2004 | Mullaney ...................... 606/59 |
| 2004/0092930 A1 * | 5/2004 | Petit et al. ..................... 606/61 |
| 2005/0113830 A1 * | 5/2005 | Rezach et al. ................ 606/60 |
| 2006/0217718 A1 * | 9/2006 | Chervitz et al. .............. 606/61 |
| 2006/0247628 A1 * | 11/2006 | Rawlins et al. ............... 606/61 |
| 2006/0253118 A1 * | 11/2006 | Bailey ........................... 606/61 |
| 2007/0055239 A1 * | 3/2007 | Sweeney et al. .............. 606/61 |
| 2007/0156142 A1 * | 7/2007 | Rezach et al. ................ 606/61 |
| 2007/0173833 A1 * | 7/2007 | Butler et al. .................. 606/61 |

(Continued)

*Primary Examiner* — Eduardo C Robert
*Assistant Examiner* — Stuart S Bray

(57) ABSTRACT

A spinal connector assembly includes a connector body having a first receiver portion, a second receiver portion, and a threaded portion extending axially from the second receiver portion. A washer member coupled with the connector may rotate about the rotational axis and translate along the rotational axis. A lock member threadingly engages the threaded portion of the connector body to exert an axial force onto a second implant member to compress the second implant member within a channel in the washer member which in turn displaces the washer member into compressed engagement with a first implant member to thereby lock the washer member and the second implant member at a select angular orientation relative to the connector body, and the axial force also compresses the first implant member into clamped engagement within the first passage of the connector body.

27 Claims, 7 Drawing Sheets

U.S. PATENT DOCUMENTS

| | | | |
|---|---|---|---|
| 2007/0293861 A1* | 12/2007 | Rezach et al. | 606/61 |
| 2009/0076549 A1* | 3/2009 | Lim et al. | 606/246 |
| 2009/0163962 A1* | 6/2009 | Dauster et al. | 606/305 |
| 2009/0234391 A1* | 9/2009 | Butler et al. | 606/278 |
| 2010/0160971 A1* | 6/2010 | Glerum et al. | 606/278 |
| 2010/0198260 A1* | 8/2010 | Gabelberger et al. | 606/264 |
| 2010/0292735 A1* | 11/2010 | Schlaepfer et al. | 606/278 |
| 2010/0324606 A1* | 12/2010 | Moskowitz et al. | 606/300 |
| 2011/0137347 A1* | 6/2011 | Hunziker | 606/258 |
| 2011/0196425 A1* | 8/2011 | Rezach et al. | 606/278 |
| 2012/0029571 A1* | 2/2012 | Schwab et al. | 606/278 |

* cited by examiner

SPINAL CONNECTOR ASSEMBLY

BACKGROUND

Spinal implants can be engaged to or along one or more vertebrae of the spinal column for the treatment of various spinal conditions or abnormalities. Elongate rods are commonly used to stabilize and support portions of the spinal column for treatment, either by fixing the spinal column or by permitting at least some degree of relative motion between the stabilized motion segments. Bone anchors such as, for example, bone screws are provided to secure the elongate rods to one or more vertebrae at a particular location along the spinal column. In some instances, connectors or other types of coupling devices are used to interconnect the rods with the bone anchors. Current connectors and coupling devices typically have a large footprint or outer profile, include numerous pieces that are not particularly easy to use or assemble, and/or are not sufficiently adjustable to accommodate for variations in the position and/or angular orientation of the bone anchors relative to the elongate rods. Thus, there remains a need in the art for a spinal connector assembly that provides advantages over existing connector or coupling devices.

SUMMARY

The present invention relates generally to a connector assembly, and more particularly but not exclusively relates to a spinal connector assembly that accommodates for variations in the angular orientation of a bone anchor relative to an elongate support member.

According to one form of the invention, a connector assembly is provided for interconnecting first and second implant members. The connector assembly generally includes a connector body, a washer member, and a lock member. The connector body extends generally along a rotational axis and includes first and second receiver portions and a threaded portion extending axially from the second receiver portion, with the first receiver portion defining a first passage therethrough sized to receive a portion of the first implant member, and the second receiver portion defining a second passage therethrough sized to receive a portion of the second implant member. The washer member includes a first end, an opposite second end, and an axial passage extending therethrough from the first end to the second end. The second receiver portion of the connector body is positioned within the axial passage in the washer member and is movably coupled with the washer member to permit rotational movement of the washer member about the rotational axis and translational movement of the washer member along the rotational axis. The washer member also includes a channel extending transversely therethrough in communication with the axial passage and generally aligned with the second passage of the connector body. The lock member is threadingly engaged with the threaded portion of the connector body such that threading engagement of the lock member along the threaded portion of the connector body exerts an axial force onto the second implant member positioned within the second passage of the connector body to thereby compress the second implant member within the channel in the washer member, and wherein the axial force displaces the washer member along the rotational axis and into compressed engagement with the first implant member positioned within the first passage of the connector body to thereby lock the washer member and the second implant member at a select angular orientation relative to the connector body, and the axial force also compresses the first implant member into clamped engagement against the first receiver portion of the connector body to thereby lock the first implant member within the first passage of the connector body.

According to another form of the invention, a connector assembly is provided for interconnecting first and second implant members. The connector assembly generally includes a connector body, a washer member, a nut member, and a drive member. The connector body extends generally along a rotational axis and includes first and second receiver portions and an externally threaded stem portion extending axially from the second receiver portion, with the first receiver portion defining a first passage therethrough sized to receive a portion of the first implant member, and the second receiver portion defining a second passage therethrough sized to receive a portion of the second implant member. The washer member includes a first end, an opposite second end, and an axial passage extending therethrough from the first end to the second end. The second receiver portion of the connector body is positioned within the axial passage in the washer member and is movably coupled with the washer member to permit rotational movement of the washer member about the rotational axis and translational movement of the washer member along the rotational axis. The washer member also includes a channel extending transversely therethrough in communication with the axial passage and generally aligned with the second passage of the connector body. The nut member is threadingly engaged with the externally threaded stem portion of the connector body and includes a first series of drive teeth extending about a perimeter thereof. The drive member includes a distal drive portion having a second series of drive teeth extending about a drive axis and rotatingly intermeshed with the first series of drive teeth defined by the nut member whereby rotation of the distal drive portion about the drive axis correspondingly rotates the nut member about the rotational axis and threadingly advances the nut member along the stem portion of the connector body, wherein threading advancement of the nut member along the stem portion exerts an axial force onto the second implant member positioned within the second passage of the connector body to thereby compress the second implant member within the channel in the washer member, and wherein the axial force displaces the washer member along the rotational axis and into compressed engagement with the first implant member positioned within the first passage of the connector body to thereby lock the washer member and the second implant member at a select angular orientation relative to the connector body, and the axial force also compresses the first implant member into clamped engagement against the first receiver portion of the connector body to thereby lock the first implant member within the first passage of the connector body.

Further forms, embodiments, features, aspects, benefits, objects and advantages of the spinal connector assembly will become apparent from the detailed description and figures provided herewith.

DESCRIPTION OF THE ILLUSTRATED EMBODIMENTS

Figure 1:
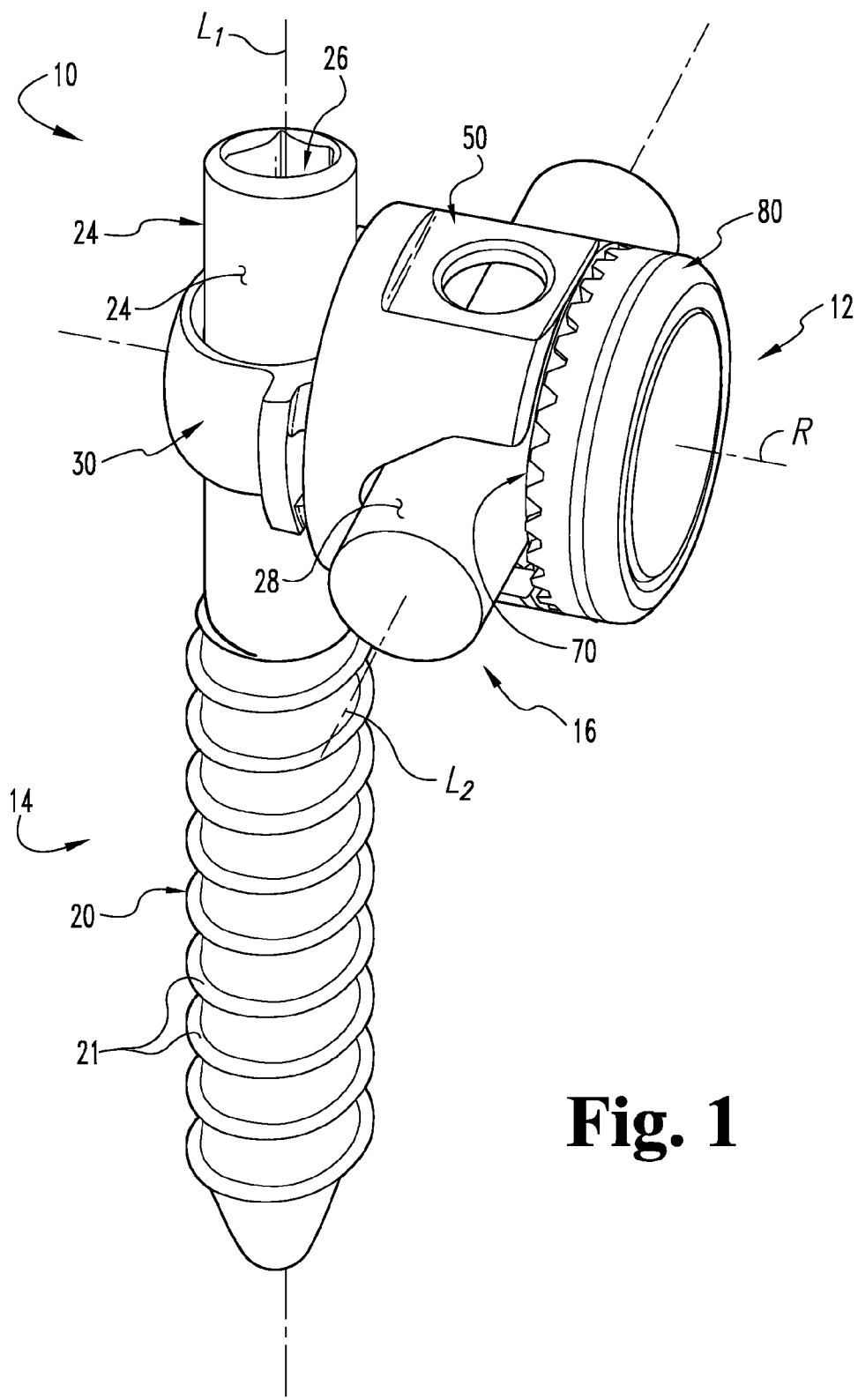
FIG. 1 is a perspective view of a spinal connector assembly according to one form of the present invention.

For the purposes of promoting an understanding of the principles of the invention, reference will now be made to the embodiments illustrated in the drawings and specific language will be used to describe the same. It will nevertheless be understood that no limitation on the scope of the invention is intended. Any alterations and further modifications in the illustrated devices and described methods and further applications of the principles of the invention as disclosed herein are contemplated as would normally occur to one skilled in the art to which the invention relates.

Referring to FIG. 1, shown therein is spinal stabilization system 10 according to one form of the present invention. The spinal stabilization system 10 generally includes an adjustable spinal connector assembly 12 extending generally along a rotational axis R and which is configured to interconnect a bone anchor member 14 extending generally along a first longitudinal axis $L_1$ with an elongate support member 16 extending generally along a second longitudinal axis $L_2$ that is laterally offset from and arranged transverse to the first longitudinal axis $L_1$.

As will be discussed in greater detail below, in the illustrated embodiment, the bone anchor member 14 comprises a bone screw and the elongate support member 16 comprises a spinal rod. However, other types and configurations of the bone anchor member 14 and the elongate support member 16 are also contemplated for use in association with the present invention. Additionally, it should be understood that the connector assembly 12 may be used to interconnect various types and configurations of spinal implants or devices, and is not limited to interconnecting a bone anchor member with an elongate support member. For example, the connector assembly 12 may alternatively be used to interconnect a pair of elongate support members, interconnect a bone anchor member with a stem associated with a coupling device, interconnect an elongate support member with a stem associated with a coupling device, or interconnect other types and configurations of spinal implants or devices. It should also be understood that the connector assembly 12 may be used in fields outside of the spinal field including, for example, in fixation or stabilization systems that are attached to other bony structures including the pelvis, the skull and/or the occiput, long bones, or other bony structures that would occur to those having ordinary skill in the art.

Figure 2:
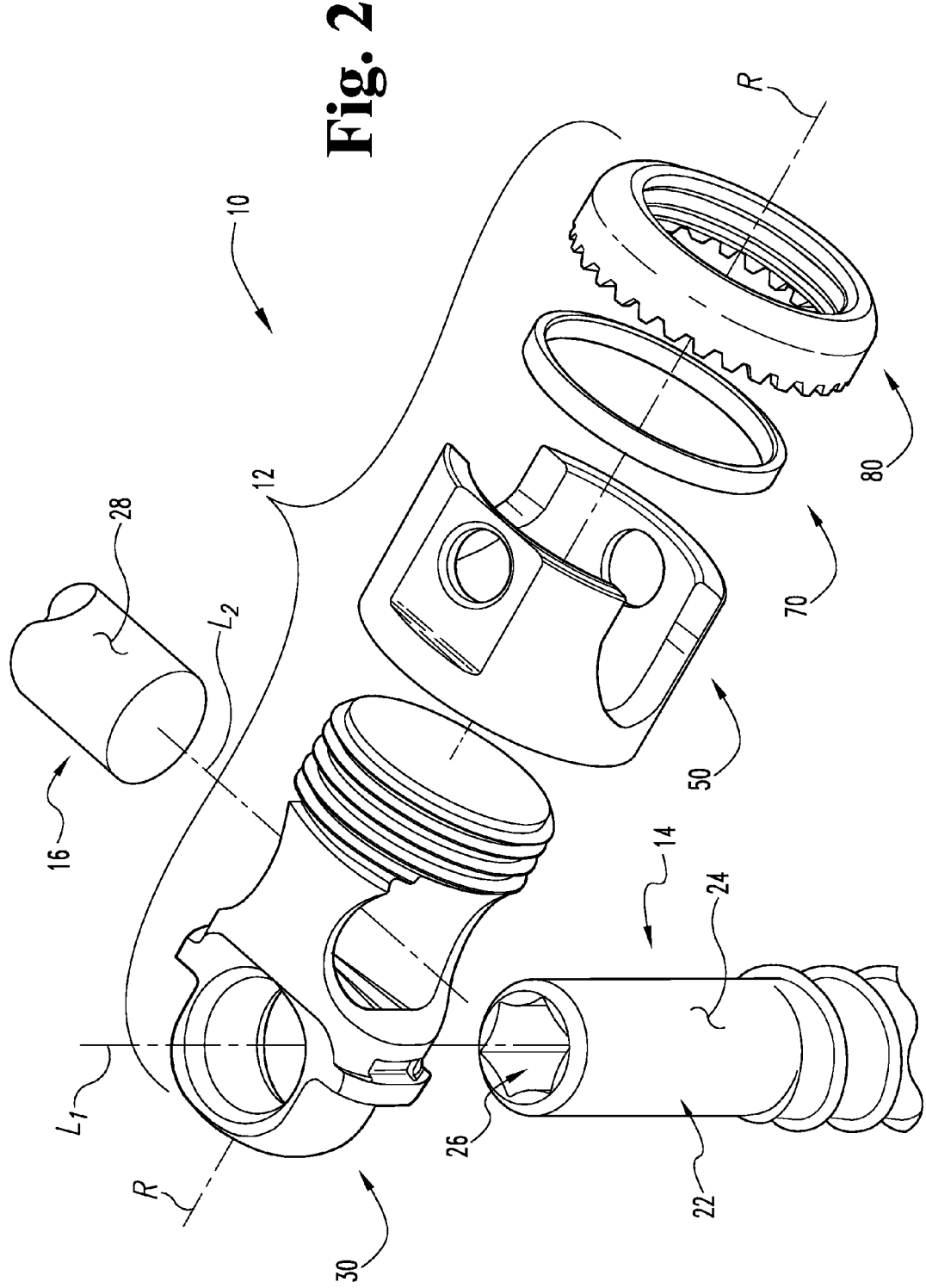
FIG. 2 is an exploded perspective view of the spinal connector assembly illustrated in FIG. 1.

Referring collectively to FIGS. 1 and 2, in the illustrated embodiment, the connector assembly 12 generally includes a housing or connector body 30, a collar or washer member 50, a spacer or ring member 70, and a nut or lock member 80. As will be discussed in greater detail below, the connector body 30 is configured to interconnect the bone anchor member 14 with the elongate support member 16. Additionally, the washer member 50, the ring member 70, and the lock member 80 cooperate with the connector body 30 and with one another to lock the connector body 30 at a particular angular orientation relative to the washer member 50 along the rotational axis R, which correspondingly locks the bone anchor member 14 at a particular angular orientation relative to the elongate support member 16. The components and elements of the spinal stabilization system 10 may be formed of various biocompatible materials including, for example, stainless steel, titanium, ceramics, plastics such as PEEK, or any other biocompatible material know to those having ordinary skill in the art.

In the illustrated embodiment, the bone anchor member 14 generally includes a distal bone engaging portion 20 and a proximal connecting portion 22. In one particular embodiment, the bone anchor member 14 is configured as a bone screw, and more particularly as a Schanz-type bone screw where the bone engaging portion 20 is configured as a threaded shank including bone engaging threads 21 adapted for anchoring in bone, and where the proximal connecting portion 22 is configured as a cylindrical-shaped head or post including a substantially circular and smooth outer surface 24 having a generally uniform outer diameter that is substantially equal to the root diameter of the bone engaging threads 21. However, it should be understood that the proximal connecting portion 22 may be provided with other shapes and configurations and may be roughened or textured to facilitate secure connection with the connector assembly 12. The connecting portion 22 is also provided with a tool engaging feature 26 configured for releasable engagement with a driver instrument (not shown) to facilitate driving of the bone anchor member 14 into bone. In the illustrated embodiment, the tool engaging feature 26 comprises a tool receiving recess or print extending axially into the connecting portion 22 from a proximal end thereof, and which is sized and configured to receive a distal end portion of a driver instrument therein. In one embodiment, the tool receiving recess 26 has a hexagonal configuration, although other shapes are also contemplated. It should also be understood that other types and configurations of tool engaging features are also contemplated including, for example, a tool engaging projection or stem extending axially from the proximal end of the connecting portion 22. It should further be understood that other types and configurations of bone screws are also contemplated including, for example, bone screws having other thread configurations and/or other types of proximal connecting portions. Additionally, other types and configurations of bone anchor members are also contemplated for use in association with the present invention including, for example, hooks, pins, bolts, clamps, staples, interbody devices, or any other type of bone anchor device know to those having ordinary skill in the art.

In the illustrated embodiment, the elongate support member 16 is configured as a spinal rod including a substantially smooth outer surface 28 defining a circular outer cross section having a substantially uniform outer diameter. However, it should be understood that the elongate support member 16 may be provided with other cross sectional shapes, and the outer surface 28 may be roughened (e.g., via knurling or threading) or otherwise textured to facilitate secure connection with the connector assembly 12. It should also be understood that other types and configurations of elongate support members are also contemplated for use in association with the present invention including, for example, bars, elongate plates, wires, tethers, or any other type of elongate support member know to those having ordinary skill in the art.

Figure 3:
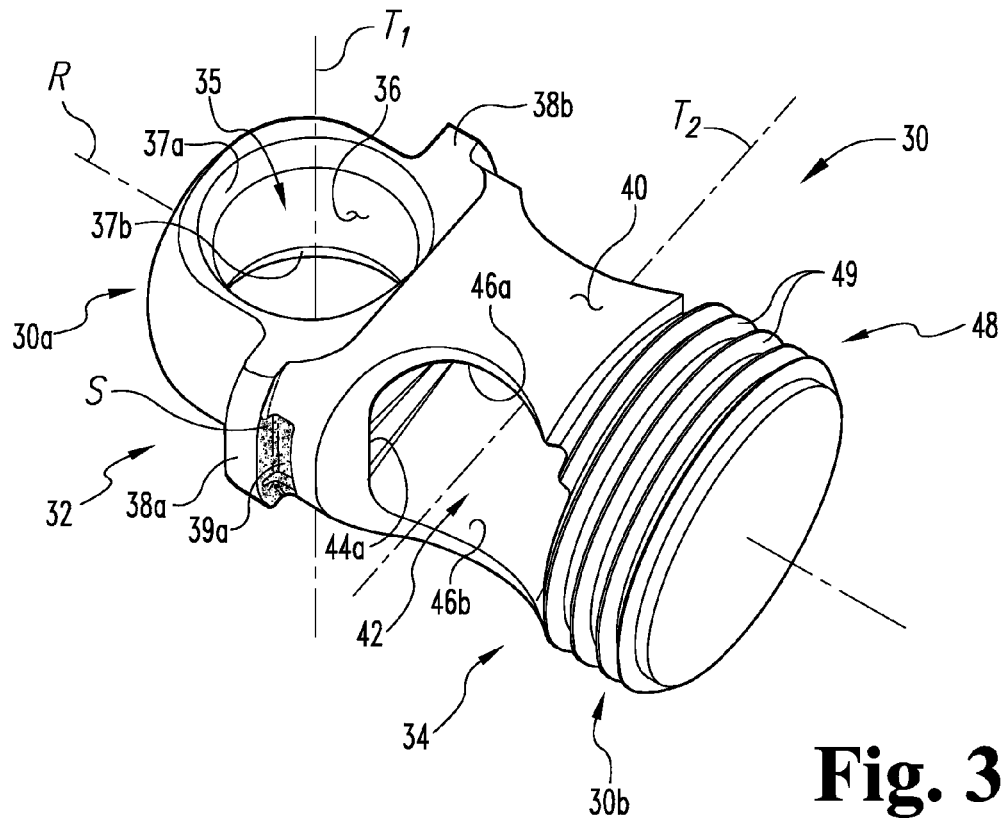
FIG. 3 is an enlarged perspective view of the connector member included in the spinal connector assembly illustrated in FIG. 1.

Referring to FIG. 3, shown therein are further details associated with the housing or connector body 30. In the illustrated embodiment, the connector body 30 extends generally along the rotational axis R from a first end 30a to an opposite second end 30b, and generally includes a bone anchor or screw receiving portion 32 and a support member or rod receiving portion 34. The screw receiving portion 32 and the rod receiving portion 34 are axially offset from one another along the rotational axis R. In one embodiment, the screw receiving portion 32 and the rod receiving portion 34 are formed unitarily integral with one another to provide the connector body 30 as a solid body core or a monolithic single-piece structure where the screw receiving portion 32 and the rod receiving portion 34 are non-movable relative to one another. However, other configurations of the connector body 30 are also contemplated where the screw receiving portion 32 and the rod receiving portion 34 are formed separately and coupled to one another by a connection mechanism, either in a rigid, non-movable embodiment or in an embodiment wherein the screw receiving portion 32 and the rod receiving portion 34 are movably coupled to one another to allow relative translational movement therebetween generally along or transverse to the rotational axis R and/or relative rotational movement therebetween about the rotational axis R.

In the illustrated embodiment, the screw receiving portion 32 has a generally cylindrical shape extending along a transverse axis $T_1$ and defining a screw receiving passage 35 extending through the screw receiving portion 32 and also arranged generally along the transverse axis $T_1$. In one embodiment, the screw receiving passage 35 has a circular shape and includes a cylindrical shaped inner surface 36 defining an inner diameter sized somewhat larger but in relatively close tolerance with the outer diameter of the proximal connecting portion 22 of the bone anchor member 14, and with the upper and lower end portions of the passage 35 defining a tapered or angled inner surface 37a, 37b extending from the cylindrical shaped inner surface 36 to facilitate insertion of the proximal connecting portion 22 of the bone anchor member 14 into the screw receiving passage 35. However, other shapes and configurations of the screw receiving passage 35 are also contemplated including, for example, an oblong or elongate slot configuration to allow the bone anchor member 14 to be translationally displaced within the screw receiving passage 35 along the rotational axis R or in a direction transverse to the rotational axis R. Additionally, in other embodiments, the inner surface 36 defining the screw receiving passage 35 may inwardly taper toward a mid-portion of the passage 35 so as to define one or more protruding portions extending transversely into the passage to permit angular displacement or pivotal movement of the proximal connecting portion 22 of the bone anchor member 14 within the passage 35 relative to the transverse axis $T_1$. In still other embodiments, one or more portions of the inner surface 36 of the passage 35 may define convex or concave portions and/or may be at least partially conical shaped or at least partially spherical shaped.

In one embodiment, the screw receiving portion 32 further includes a pair of flanges or lips 38a, 38b positioned on opposite sides of the screw receiving passage 35 and extending in a direction generally perpendicular or normal to the transverse axis $T_1$ and the rotational axis R. The screw receiving portion 32 of the connector body 30 further includes a pair of recesses or pockets 39a, 39b arranged on opposite sides of the passage 35 and positioned axial adjacent respective ones of the flanges 38a, 38b on the side of the flanges 38a, 38b opposite the screw receiving passage 35. The recesses or pockets 39a, 39b may be at least partially filled with a flexible spacer element S, the purpose of which will be discussed below. In one embodiment, the flexible spacer element S comprises silicone material or a silicone spacer. However, other types of spacer elements and spacer materials are also contemplated as would occur to those skilled in the art.

In the illustrated embodiment, the rod receiving portion 34 has a generally cylindrical shape and includes a circumferential or cylindrical shaped outer surface 40 extending about the rotational axis R. As will be discussed in greater detail below, the cylindrical or circular shaped outer surface 40 is sized and configured for receipt within an axial passage extending through the washer member 50. The rod receiving portion 34 also defines a rod receiving passage 42 extending through the rod receiving portion 34 and arranged generally along a transverse axis $T_2$. In one embodiment, the transverse axis $T_2$ of the rod receiving passage 42 is offset from and arranged substantially perpendicular or normal to the transverse axis $T_1$ of the screw receiving passage 35. However, other embodiments are also contemplated where the transverse axes $T_1$, $T_2$ are arranged substantially in the same plane and/or are arranged at an oblique angle relative to one another. In still other embodiments, the transverse axes $T_1$, $T_2$ may be arranged generally parallel to one another. As shown in the cross-sectional view of FIG. 9, in the illustrated embodiment, the rod receiving passage 42 has a generally rectangular configuration including a pair of opposing side surfaces 44a, 44b, a pair of opposing upper and lower surfaces 46a, 46b, and rounded corner surfaces 45 extending from the side surfaces 44a, 44b to the upper and lower surfaces 46a, 46b. However, other configurations of the rod receiving passage 42 are also contemplated including, for example, a circular configuration, an elongated slot configuration, an oval or elliptical configuration, or other configurations that would be apparent to those having ordinary skill in the art.

In the illustrated embodiment, the connector body 30 further includes a threaded stem portion 48 extending axially from the rod receiving portion 34 generally along the rotational axis R and defining external threads 49. In the illustrated embodiment, the external threads 49 on the stem portion 48 are configured as left-hand threads. However, in another embodiment, the external threads 49 on the stem portion 48 may alternatively be configured as right-hand threads. Additionally, in the illustrated embodiment, the rod receiving passage 40 partially intersects the threaded stem portion 48 and interrupts a portion of the external threads 49. As will be discussed in greater detail below, the threaded stem portion 48 is sized and configured for threading engagement with the nut or lock member 80. In one embodiment, the threaded stem portion 48, the rod receiving portion 34, and the screw receiving portion 32 are formed unitarily integral with one another to provide the connector body 30 as a solid body core or a monolithic single-piece structure where the threaded stem portion 48, the rod receiving portion 34, and the screw receiving portion 32 are non-movable relative to one another. However, other configurations of the connector body 30 are also contemplated where the threaded stem portion 48, the rod receiving portion 34, and/or the screw receiving portion 32 are formed separately and coupled to one another by a connection mechanism, either in a rigid, non-movable embodiment or in an embodiment wherein one or more of these components are movably coupled to one another to allow relative translational movement therebetween and/or relative rotational movement therebetween.

Figure 4:
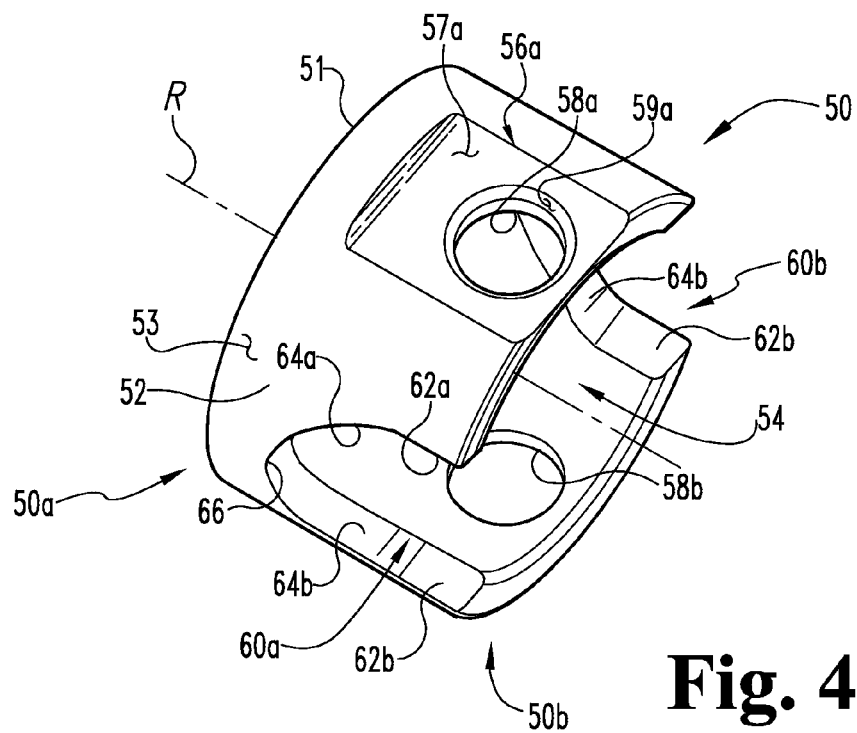
FIG. 4 is an enlarged perspective view of the washer member included in the spinal connector assembly illustrated in FIG. 1.

Referring to FIG. 4, shown therein are further details associated with the collar or washer member 50. In the illustrated embodiment, the washer member 50 has a cylindrical configuration defining a generally circular outer cross section extending from a first end 50a to a second end 50b. The washer member 50 generally includes an end wall 51, a cylindrical-shaped side wall 52, and a hollow interior defining an axial passage 54 extending from the first end 50a, through the end wall 51, and along the side wall 52 to the second end 50b. The side wall 52 has a generally circular or cylindrical outer surface 53 and defines a pair of truncated regions 56a, 56b arranged opposite one another and defining flat or planar surfaces 57a, 57b, respectively, and a pair of circular-shaped apertures 58a, 58b extending through the truncated regions 56a, 56b, respectively, and in communication with the axial passage 54. The outer end portions of the apertures 58a, 58b adjacent the flat/planar surface 57a, 57b define tapered or angled surface 59a, 59b to facilitate insertion of a distal end portion of a driving member (FIG. 10) into the apertures 58a, 58b.

Figure 8:
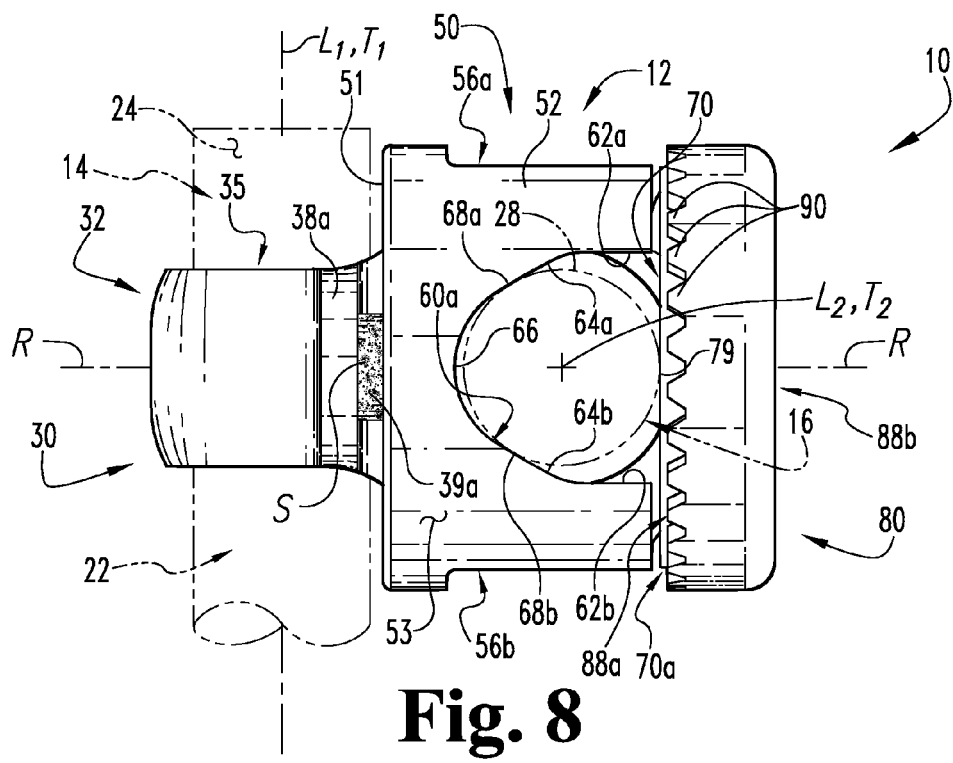
FIG. 8 is a side view of the spinal connector assembly illustrated in FIG. 1.
Figure 9:
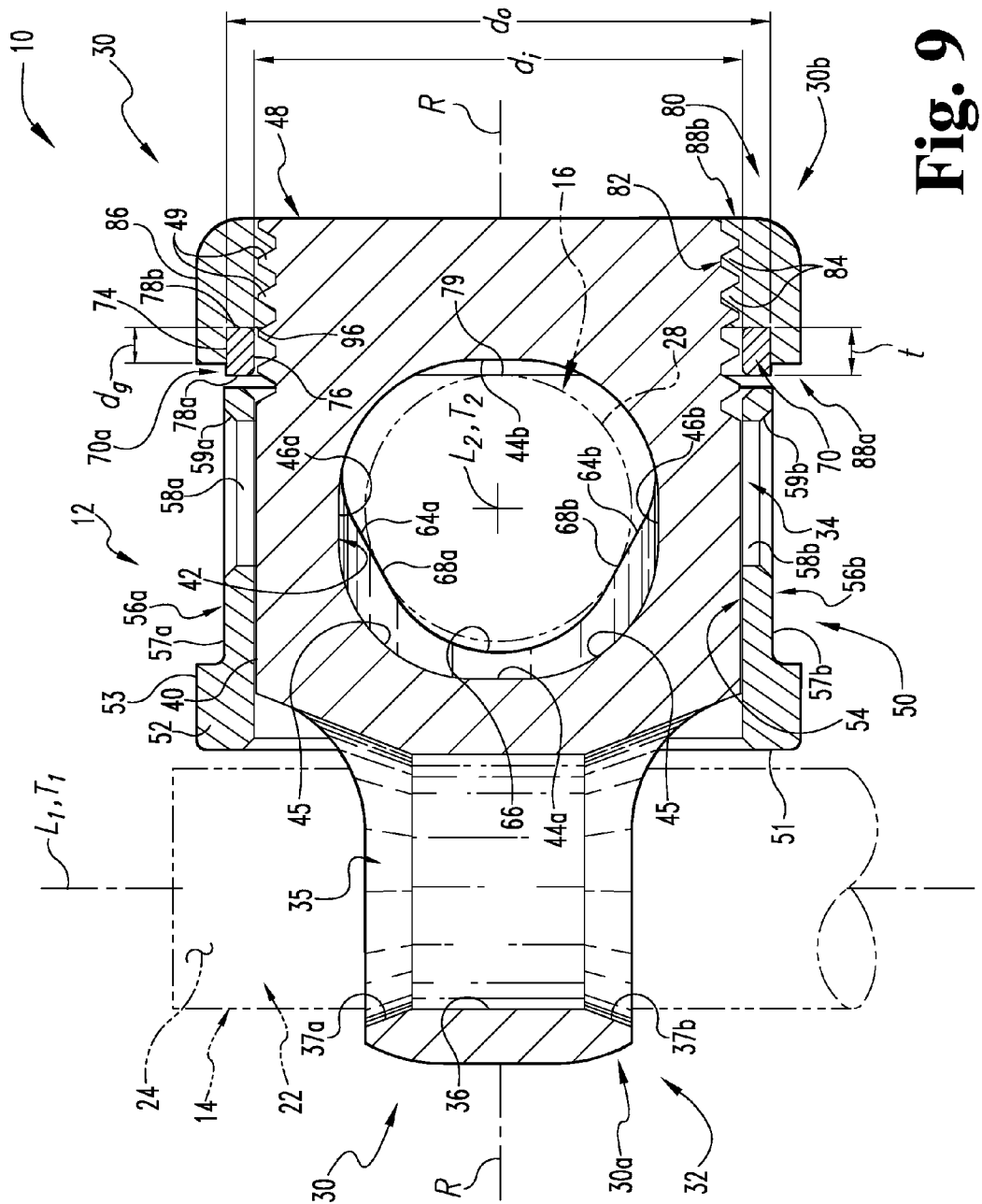
FIG. 9 is a cross sectional side view of the spinal connector assembly illustrated in FIG. 1, as taken along line 9-9 of FIG. 7.

In the illustrated embodiment, the washer member 50 further defines a pair of channels or slotted openings 60a, 60b extending from the second end 50b toward the first end 50a. The slotted opening 60a, 60b are configured substantially identical to one another, are arranged generally opposite one another, and are positioned between the truncated regions 56a, 56b. As shown in FIGS. 8 and 9, the channels 60a, 60b each include a pair of generally parallel flat surface regions 62a, 62b extending from the second end 50b toward the first end 50a along the rotational axis R, a pair of angled surface regions 64a, 64b extending from the flat surface regions 62a, 62b and tapering inwardly toward one another along the rotational axis R toward the first end 50a, and a circular surface region 66 extending between the ends of the angled surface regions 64a, 64b. As shown in FIG. 8, the elongate support member 16 and the channels 60a, 60b are sized such that when fully engaged within the channels 60a, 60b, two points of direct contact 68a, 68b are defined between the outer surface 28 of the elongate support member 16 and the angled surface regions 64a, 64b. Although a particular shape and configuration of the channels 60a, 60b have been set forth herein, it should be understood that other shapes and configurations of the channels 60a, 60b are also contemplated.

In the illustrated embodiment, the washer member 50 is configured as a single-piece washer. However, in other embodiments, the washer member 50 may be provided as a two-piece washer, with the two washer pieces independently rotatable about the connector body 30 and which may be selectively rotationally interlocked together via a series of intermeshing radial splines defined by opposing end surfaces of the washer pieces, or via interlocking engagement of taper lock elements defined by opposing surfaces of the washer pieces. In embodiments utilizing a two-piece washer design, the first washer piece may be configured similar to the washer member 50, and with the second washer piece positioned between the first washer piece and the proximal post 22 of the bone anchor member 14. In this manner, the second washer piece may be engaged with the proximal post 22 of the bone anchor member 14 and maintained in a stationary rotational position, whereas the first washer piece may be rotated about the connector body 30 to position the elongate support member 16 at a select angular orientation relative to the bone anchor member 14. The first and second washer pieces may thereafter be rotationally engaged and interlocked with one another to prevent further rotational movement therebetween, which in turn locks the elongate support member 16 at the select angular orientation relative to the bone anchor member 14.

Figure 5:
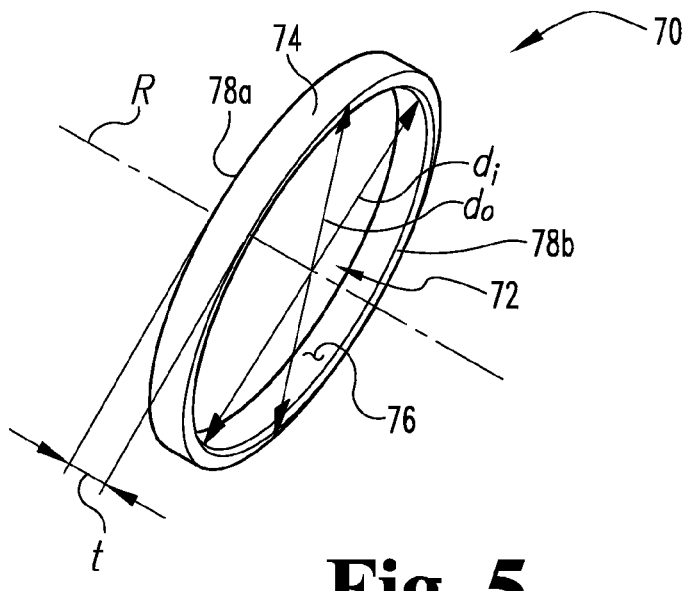
FIG. 5 is an enlarged perspective view of the ring member included in the spinal connector assembly illustrated in FIG. 1.

Referring to FIG. 5, shown therein are further details associated with the spacer or ring member 70. In the illustrated embodiment, the ring member 70 has an annular ring-shaped configuration defining a central aperture 72 extending therethrough and including an outer circumferential or cylindrical shaped surface 74 extending about the rotational axis R and defining an outer ring diameter $d_o$, and an inner circumferential or cylindrical shaped surface 76 extending about the rotational axis R and defining an inner ring diameter $d_i$. The ring member 70 further includes oppositely facing end surfaces 78a, 78b defining a ring thickness t therebetween. Although the ring member 70 is illustrated as having an annular or circular configuration, it should be understood that other shapes and configurations of the ring member 70 are also contemplated.

Figure 6:
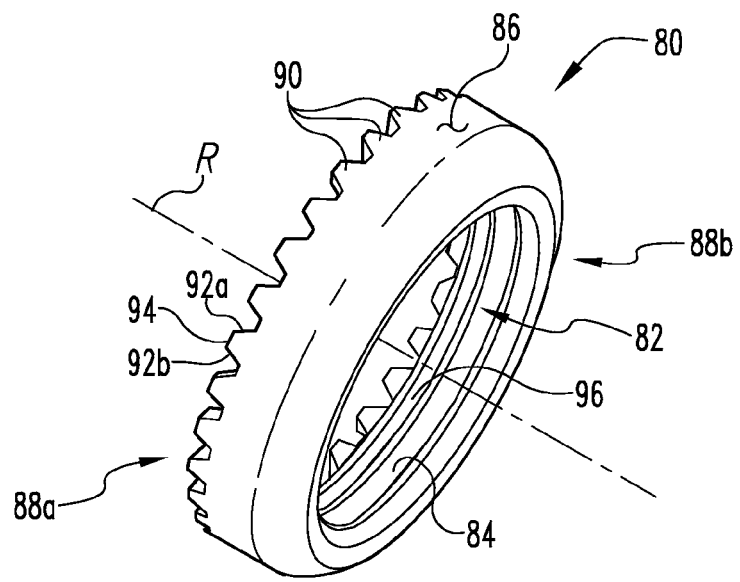
FIG. 6 is an enlarged perspective view of the lock member included in the spinal connector assembly illustrated in FIG. 1.

Referring to FIG. 6, shown therein are further details associated with the nut or lock member 80. In the illustrated embodiment, the lock member 80 has an annular ring-shaped configuration and is configured as a nut defining a threaded central passage 82 extending therethrough along the rotational axis R and defining internal threads 84 configured for threading engagement with the external threads 49 formed along the threaded stem portion 48 of the connector body 30. In the illustrated embodiment, the internal threads 84 formed along the central passage 82 are configured as left-hand threads so that counter clockwise rotation of the lock member 80 advances the lock member 80 along the threaded stem portion 48 in the direction of the rod receiving passage 42. However, in another embodiment, the internal threads 84 formed along the central passage 82 and the external threads 49 formed along the threaded stem portion 48 of the connector body 30 may alternatively be configured as right-hand threads so that clockwise rotation of the lock member 80 advances the lock member 80 along the threaded stem portion 48 in the direction of the rod receiving passage 42. The lock member 80 further includes an outer circumferential or cylindrical shaped surface 86 extending about the rotational axis R and defining an outer diameter substantially corresponding to that of the outer diameter of the washer member 50. Although the lock member 80 is illustrated as having an annular and circular configuration, it should be understood that other shapes and configurations of the lock member 80 are also contemplated.

In the illustrated embodiment, the lock member 80 has oppositely facing end surfaces 88a, 88b, with the end surface 88a including a series of splines or gear/drive teeth 90 formed about the end surfaces 88a and extending from the end surface 88a in a direction generally along the rotational axis R, the purpose of which will be discussed below. In the illustrated embodiment, the splines or gear/drive teeth 90 each have leading and trailing angled flank surfaces 92a, 92b extending to a generally planar outer crest surface 94. The lock member 80 also defines an inner annular groove or notch 96 extending about the passage 82 adjacent the end surface 88a which defines the splines or gear/drive teeth 90. As illustrated in FIG. 9, the annular groove 96 defines an inner diameter closely corresponding to the outer diameter $d_o$ of the ring member 70 to provide a relatively close fit between the lock member 80 and the ring member 70, and the annular groove 96 defines a groove depth $d_g$ sized somewhat less than the thickness t of the ring member 70 so that an end portion 70a of the ring member 70 extends beyond the splines or gear/drive teeth 90 of the lock member 80. Although the lock member 80 has been illustrated as an annular nut, other types and configurations of the lock member 80 are also contemplated for use in association with the present invention, including embodiments that are not configured as an internally threaded nut but which are nevertheless configured to be movably engaged along the stem portion 48 of the connector body 30 for displacement generally along the rotational axis R.

Figure 7:
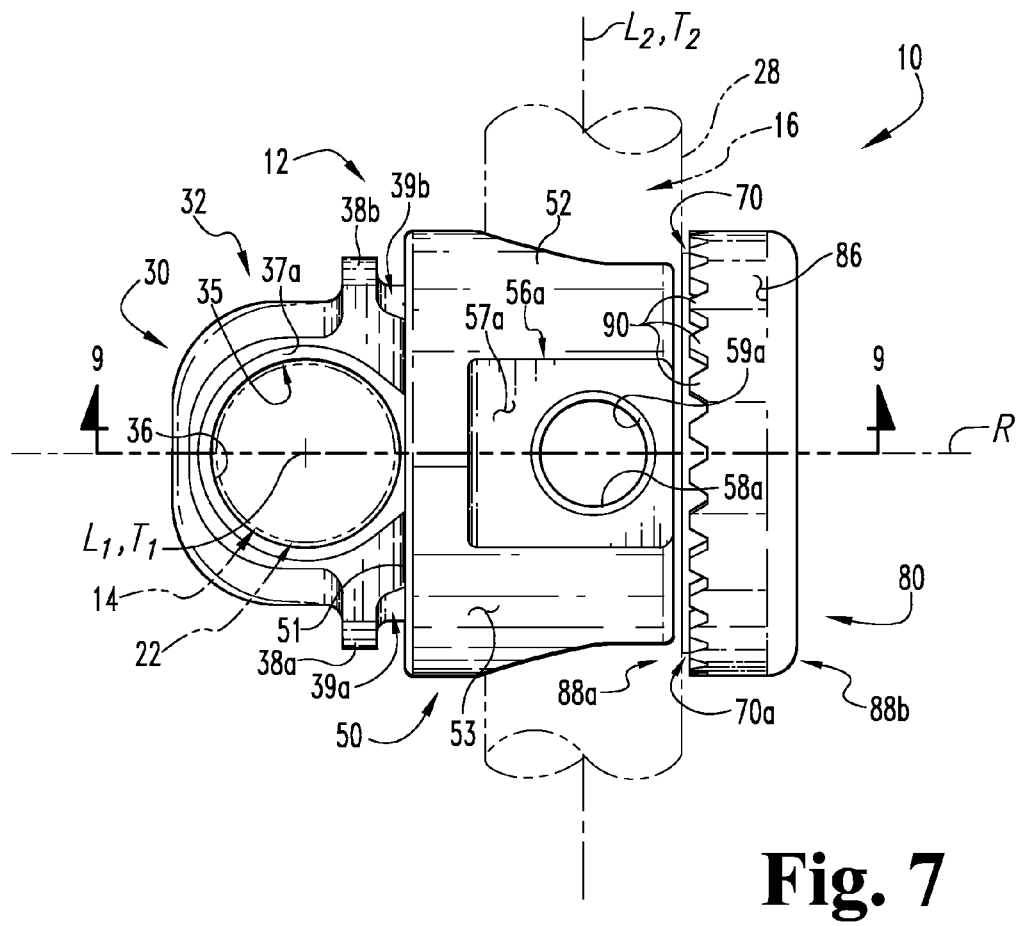
FIG. 7 is a top view of the spinal connector assembly illustrated in FIG. 1.

Referring collectively to FIGS. 7-9, shown therein are various views of the connector assembly 12 which illustrate further details regarding the relationship and interaction between the components of the connector assembly 12 and their relation to the bone anchor member 14 and the elongate support member 16.

Having described the components, elements and features associated with the connector assembly 12, reference will now be made to one embodiment of assembling the connector assembly 12 and engaging the connector assembly 12 to the bone anchor member 14 and the elongate support member 16. However, it should be understood that the assembly steps are exemplary and that other embodiments of assembling the connector assembly 12 and engaging the connector assembly 12 to the bone anchor member 14 and the elongate support member 16 are also contemplated as falling within the scope of the invention.

The connector assembly 12 is initially assembled by inserting the rod receiving portion 34 of the connector body 30 through the opening in the end wall 51 of the washer member 50 and into the axial passage 54 until the flanges 38a, 38b of the connector body 30 are positioned adjacent the end wall 51 of the washer member 50, and with the channels 60a, 60b in the washer member 50 generally aligned with the rod receiving passage 42 in the connector body 30 along the transverse axis $T_2$. The end wall 51 of the washer member 50 is provisionally spaced from the flanges 38a, 38b via the flexible spacer element S (FIG. 8) positioned within the pockets 39a, 39b adjacent the flanges 38a, 38b, which in turn provisionally prevents the end wall 51 of the washer member 50 from partially covering the screw receiving passage 35 in the screw receiving portion 32 of the connector body 30 to allow insertion of the proximal connecting portion 22 of the bone anchor member 14 into the screw receiving passage 35.

The ring member 70 is positioned within the annular groove 96 in the lock member 80. As indicated above, the inner diameter of the annular groove 96 is sized in close tolerance with the outer diameter $d_o$ of the ring member 70 to provide a relatively close fit therebetween to maintain engagement of the ring member 70 within the annular groove 96. Additionally, the thickness t of the ring member 70 is somewhat greater than the groove depth $d_g$ of the annular groove 96 so that an end portion 70a of the ring member 70 extends beyond the splines or gear/drive teeth 90 of the lock member 80. In the illustrated embodiment, the ring member 70 and the lock member 80 comprise separate components that are assembled together to form an integrated structure. However, it should be understood that in other embodiments, the ring member 70 and the lock member 80 may be formed unitarily integral with one another so as to define a monolithic single-piece structure.

Following engagement of the ring member 70 within the annular groove 96 of the lock member 80, the lock member 80 is initially threaded onto the threaded stem portion 48 of the connector body 30 via threading engagement between the internal threads 84 of the lock member 80 and the external threads 49 of the stem portion 48 to preliminarily engage the lock member 80 to the connector body 30. As indicated above, in the illustrated embodiment, the internal threads 84 and the external threads 49 are each configured as left-hand threads. Accordingly, the lock member 80 is initially threaded onto the threaded stem portion 48 of the connector body 30 via rotation of the lock member 80 in a counter clockwise direction. However, as indicated above, a reverse configuration is also contemplated.

In one embodiment, the bone anchor member 14 is anchored to a vertebra or another bony structure via driving engagement of the threaded shank 20 into bone. The connector assembly 12 is then engaged to the proximal post 22 of the bone anchor member 14 by passing the screw receiving passage 35 in the connector body 30 over the proximal post 22. The elongate support member 16 may then be provisionally engaged with the connector assembly 12 via insertion through the channels 60a, 60b in the washer member 50 and through the rod receiving passage 42 in the connector body 30. However, it should be understood that other embodiments are also contemplated where the bone anchor member 14 and the elongate support member 16 are engaged with the connector assembly 12 in other sequences or assembly steps. For example, in another embodiment, the proximal post 22 of the bone anchor member 14 may be positioned within the screw receiving passage 35 in the connector body 30 prior to anchoring the threaded shank 20 into bone. Additionally, the elongate support member 16 may be inserted into the channels 60a, 60b in the washer member 50 and the rod receiving passage 42 in the connector body 30 prior to implantation of the connector assembly 12 into the patient and/or prior to engagement of the connector assembly 12 to the proximal post 22 of the bone anchor member 14. As should be appreciated, the particular assembly sequence of the stabilization system 10 can be modified or changed to accommodate various surgical requirements, procedures or preferences.

At this point in the assembly process of the stabilization system 10, the locking member 80 is not fully threaded/tightened onto the threaded stem portion 48 of the connector body 30, thereby defining an unlocked or loosened state of the connector assembly 12. In this unlocked or loosened state, the connector body 30 is permitted to slide vertically along the proximal post 22 of the bone anchor member 14 in the direction of arrows V (FIG. 10) to thereby adjust the dorsal height of the connector assembly 12 (and the elongate support member 16) relative to the vertebra or bone to which the bone anchor member 14 is engaged. Additionally, in the unlocked or loosened state, the washer member 50 is allowed to freely rotate relative to the connector body 30 about the rotational axis R, which in turn allows pivotal or angular displacement of the elongate support member 16 relative to the bone anchor member 14 in the direction of arrows P (FIG. 10) along a plane arranged substantially parallel with the sagittal plane of the patient. Notably, in the unlocked or loosened state of the connector assembly 12, the end wall 51 of the washer member 50 is spaced from and does not compressingly engage the proximal post 22 of the bone anchor member 14, and the end surface 78a of the ring member 70 is spaced from and does not compressingly engage the elongate support member 16, thereby allowing the washer member 50 (and the elongate support member 16) to freely rotate/pivot relative to the connector body 30 (and the bone anchor member 14).

Figure 10:
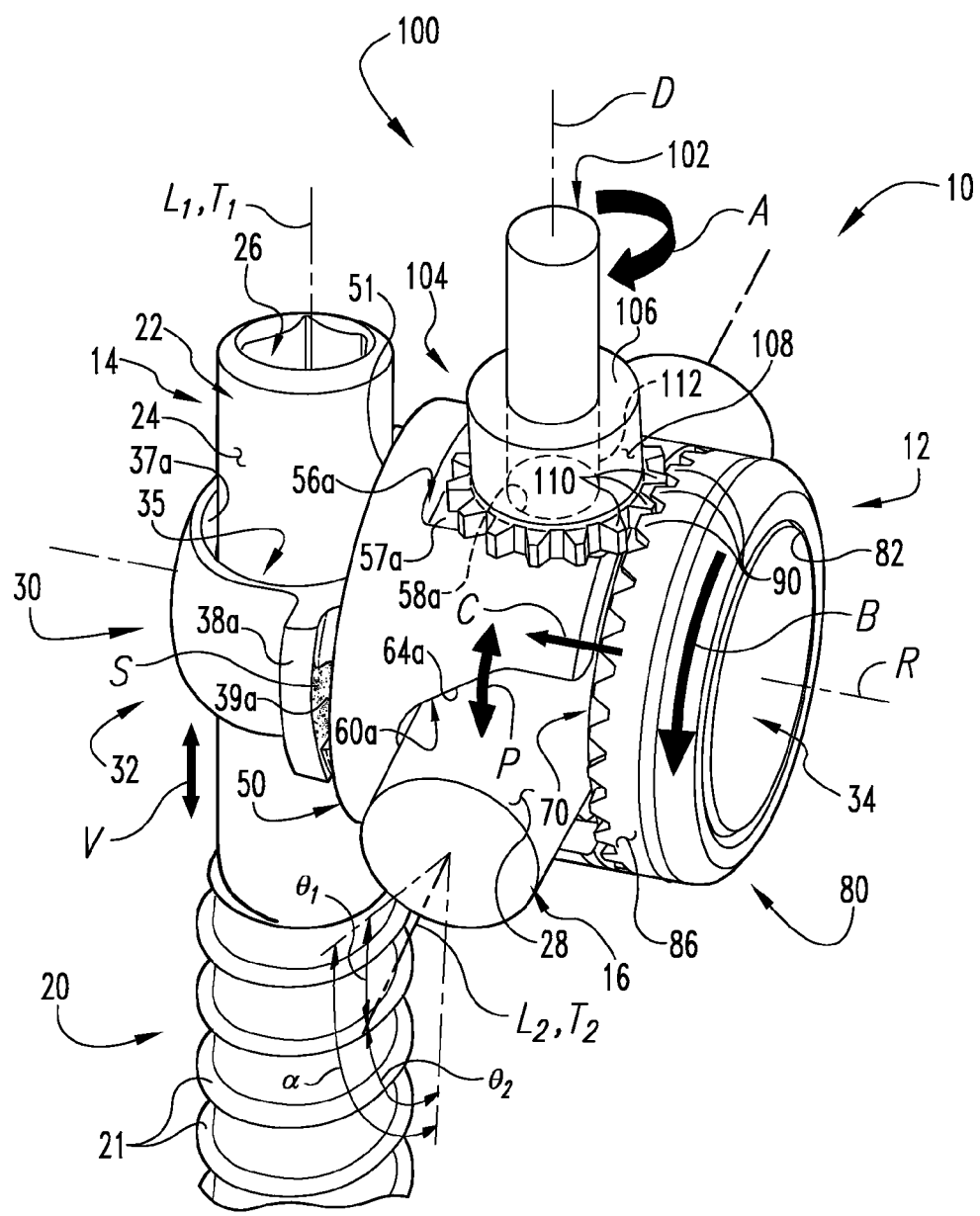
FIG. 10 is a perspective view of the spinal connector assembly illustrated in FIG. 1, as shown with one embodiment of a driving member engaged with the spinal connector assembly.

Referring now to FIG. 10, shown therein is a drive member or tool 100 according to one form of the present invention for transforming the connector assembly 12 to a locked or tightened state. In the illustrated embodiment, the drive member 100 extends along a drive axis D and generally includes a drive shaft portion 102 and a distal drive portion 104. The drive shaft portion 102 comprises a solid/rigid shaft having a generally circular outer cross section. However, other shapes and configurations of the drive shaft portion 102 are also contemplated. In one embodiment, the distal drive portion 104 is securely attached to the distal end of the drive shaft portion 102 such as, for example, by welding. However, other means for attaching the distal drive portion 104 to the drive shaft portion 102 are also contemplated as would occur to those having ordinary skill in the art. In other embodiments, the distal drive portion 104 and the drive shaft portion 102 may be formed as a unitary, single-piece structure. Although not specifically illustrated in FIG. 10, it should be understood that a rotary drive or power source such as, for example, a pneumatic or electric motor may be engaged to the drive shaft portion 102 to rotate the drive shaft portion 102 about the drive axis D, which correspondingly rotates the distal drive portion 104 about the drive axis D. However, other types and configurations of rotary drives and power sources are also contemplated. Additionally, in still other embodiments, the drive member 100 may be manually rotated by the surgeon, thereby eliminating the need for a rotary drive or power source.

The distal drive portion 104 generally includes a cylindrical-shaped body 106 defining a circular outer surface 108, and a series of splines or gear/drive teeth 110 formed about the circumference of the circular outer surface 108 and extending from the outer surface 108 in a direction generally perpendicular to the drive axis D. The splines/gear teeth 110 are configured to rotationally intermesh with the splines/gear teeth 90 formed about the lock member 80 at a right angle (i.e., the drive axis D about which the splines/gear teeth 110 are positioned is arranged substantially perpendicular to the rotational axis R about which the splines/gear teeth 90 are positioned). In the illustrated embodiment, the splines/gear teeth 110 of the distal drive portion 104 are configured substantially the same as the splines/gear teeth 90 of the lock member 80. However, in other embodiments, the splines/gear teeth 110, 90 may be configured differently from one another. The distal drive portion 104 of the drive member 100 includes a distal post or stem portion 112 that is positioned within one of the apertures 58a, 58b defined by the washer member 50 to maintain the splines/gear teeth 110 of the distal drive portion 104 in rotationally intermeshed engagement with the splines/gear teeth 90 of the lock member 80. The distal stem portion 112 is preferably sized in relatively close tolerance with the apertures 58a, 58b to maintain the drive shaft portion 102 and the distal drive portion 104 in general alignment along the drive axis D in an orientation substantially perpendicular or normal to the rotational axis R. As should be appreciated, the lower surface of the distal drive portion 104 may rest on the flat/planar surfaces 57a, 57b defined by the truncated regions 56a, 56b of the washer member 50 to stabilize the drive member 100 and to further aid in maintaining the drive shaft portion 102 and the distal drive portion 104 in an orientation substantially perpendicular or normal to the rotational axis R.

When the connector assembly 12 is in a unlocked or loosened state, the washer member 50 may be rotated relative to the connector body 30 in the direction of arrows P about the rotational axis R. Rotation of the washer member 50 relative to the connector body 30 correspondingly allows the elongate support member 16 to pivot or angulate in the direction of arrows P (in either an upward or downward direction) relative to the bone anchor member 14 along a plane arranged generally parallel with the sagittal plane of the patient until the elongate support member 16 is positioned at a select angular orientation relative to the bone anchor member 14. In the illustrated embodiment, the washer member 50 may be rotated relative to the connector body 30 about the rotational axis R to correspondingly pivot the elongate support member 16 from a substantially horizontal orientation (i.e., an orientation where the longitudinal axis $L_2$ of the elongate support member 16 is arranged substantially perpendicular to the longitudinal axis $L_1$ of the bone anchor member 14) in an upward direction to a first pivot angle $\theta_1$ and in downward direction to a second pivot angle $\theta_2$ to provide angular adjustment of the elongate support member 16 relative to the bone anchor 14 up to a total adjustment angle of $\alpha$.

In one embodiment, the elongate support member 16 may be pivoted from a substantially horizontal in an upward direction to a first pivot angle $\theta_1$ of approximately +25° and in downward direction to a second pivot angle $\theta_2$ of approximately −25° to thereby provide an overall angular adjustment up to a total adjustment angle $\alpha$ of approximately 50°. However, it should be understood that the connector assembly 12 may be configured to permit the elongate support member 16 to pivot or angulate relative to the bone anchor 14 in planes other than the sagittal plane, and to pivot to other pivot angles $\theta_1$ and $\theta_2$ and total adjustment angles $\alpha$. It should further be understood that the pivot angles $\theta_1$ and $\theta_2$ need not necessarily be equal to one another, but may instead by non-symmetrical. In a further embodiment, the connector body 30 and/or the washer member 50 may be keyed or provided with stop members or rotation limiting elements to limit rotation of the washer member 50 about the connector body 30 to the pivot angles $\theta_1$ and $\theta_2$ and the total adjustment angle $\alpha$. However, in other embodiments, the connector body 30 and/or the washer member 50 need not be provided with stop members or rotation limiting elements.

Once the connector body 30 (and the elongate support member 16) is adjusted to a desired dorsal height along the proximal post 22 of the bone anchor 14 in the direction of arrows V, and the washer member 50 (and the elongate support member 16) is positioned at a desired angular orientation relative to connector body 30 (and the bone anchor member 14), the connector assembly 12 is transitioned to a locked or tightened state to thereby secure the connector body 30 at the desired dorsal height and to secure the elongate support member 16 at the desired angular orientation. In the illustrated embodiment, the connector assembly 12 is transitioned to the locked or tightened state via rotation of the drive member 100 about the drive axis R in the direction of arrow A, which correspondingly rotates the lock member 80 about the rotational axis R in the direction of arrow B via the intermeshing rotational engagement of the splines/gear teeth 110 of the drive member 100 with the splines/gear teeth 90 of the lock member 80. In the illustrated embodiment, the direction of arrow A is a clockwise direction and the direction of arrow B is a counter clockwise direction. However, as indicated above, a reverse configuration is also contemplated.

As the lock member 80 is rotated about the rotational axis R in the direction of arrow B via rotation of the drive member 100 about the drive axis D in the direction of arrow A, the lock member 80 is threadingly advanced along the threaded stem portion 48 of the connector body 30, which in turn causes the lock member 80 to axially translate along the rotational axis R in the direction of arrow C toward the elongate support member 16. Axial translation of the lock member 80 in the direction of arrow C compressingly engages the end surface 78a of the ring member 70 against the outer surface 28 of the elongate support member 16 to form a first point of direct contact 79 with the elongate support member 16 (FIG. 8). Compression of the ring member 70 against the elongate support member 16 in turn compresses the outer surface 28 of the elongate support member 16 against the angled surface regions 64a, 64b of the channels 60a, 60b in the washer member 50 to form two additional points of direct contact 68a, 68b with the elongate support member 16 (FIG. 8). As should be appreciated, compression of the elongate support member 16 between the end surface 78a of the ring member 70 and the angled surface regions 64a, 64b of the washer member 50 locks the elongate support member 16 within the connector assembly 12 to thereby prevent further movement of the elongate support member 16 relative to the connector assembly 12. As should also be appreciated, the three points of direct contact 68a, 68b and 79 between the connector assembly 12 and the elongate support member 16 securely locks the elongate support member 16 in position within the connector assembly 12.

In the illustrated embodiment, the end surface 78a of the ring member 70 is substantially smooth and planar. However, in other embodiments, the end surface 78a may be roughened or provided with various types of engagement elements to provide an increased locking force between the ring member 70 and the elongate support member 16. In still other embodiments, the end surface 78a of the ring member 70 may be provided with a recess or cut out sized and configured for receipt of the elongate support member 16 to facilitate secure engagement of the ring member 70 with the elongate support member 16. As should be appreciated, one purpose of the ring member 70 is to prevent the splines/gear teeth 90 of the lock member 80 from directly engaging the elongate support member 16 and potentially galling, chewing into, or otherwise damaging the elongate support member 16 as the lock member 80 is rotated about the rotational axis R and advanced along the threaded stem portion 48 of the connector body 30. Another purpose of the ring member 70 is to facilitate secure engagement with the elongate support member 16.

Further tightening of the lock member 80 via rotation of the drive member 100 displaces the washer member 50 along the rotational axis R toward the proximal post 22 of the bone anchor member 14. As should be appreciated, application of a sufficient axial force onto the washer member 50 will cause the end wall 51 of the washer member 50 to pass over and be displaced beyond the flexible spacer element S positioned within the pockets 39a, 39b of the connector body 30. The end wall 51 of the washer member 50 is thereafter compressed against the proximal post 22 of the bone anchor member 14, which in turn compresses the proximal post 22 against the inner surface 36 of the screw receiving passage 35 in the connector body 30 to thereby lock the proximal post 22 of the bone anchor member 14 within the rod receiving passage 35 and prevent further movement of the proximal post 22 relative to the connector body 30. Additionally, compression of the washer member 50 between the proximal post 22 of the bone anchor member 14 and the elongate support member 16 locks the washer member 50 in a desired angular orientation relative to the connector body 30, which in turn locks the elongate support member 16 at a desired angular orientation relative to the bone anchor member 14. In the illustrated embodiment, the end wall 51 of the washer member 50 is substantially smooth and planar. However, in other embodiments, the end wall 51 may be roughened or provided with various types of engagement elements to provide an increased locking force between the washer member 50 and the proximal post 22 or the bone anchor member 14.

As should be appreciated, the unique design of the connector assembly 12 permits locking of the connector assembly 12 via a single tightening motion and a single locking member (i.e., rotation of the lock member 80 about the rotational axis R). Additionally, the unique design of the connector assembly 12 permits locking of the connector assembly 12 via a top tightening arrangement (i.e., tightening from a direction directly above the connector assembly 12). Moreover, the unique design of the connector assembly 12 minimizes the footprint or outer profile, reduces the number of connector components or pieces, provides for easy assembly and use, and is also sufficiently adjustable to accommodate for variations in the position and/or angular orientation of the elongate support member 16 relative to the bone anchor member 14.

While the invention has been illustrated and described in detail in the drawings and foregoing description, the same is to be considered as illustrative and not restrictive in character, it being understood that only the preferred embodiments have been shown and described and that all changes and modifications that fall within the spirit of the invention are desired to be protected. Additionally, any theory, mechanism of operation, proof or finding stated herein is meant to further enhance understanding of the present invention, and is not intended to make the present invention in any way dependent upon such theory, mechanism of operation, proof or finding.

It should also be understood that while the use of the word preferable, preferably or preferred in the description above indicates that the feature so described may be more desirable, it nonetheless may not be necessary, and embodiments lacking the same may be contemplated as within the scope of the application, that scope being defined by the claims that follow. In reading the claims, it is intended that when words such as "a", "an", "at least one", and "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

What is claimed is:

1. A connector assembly for interconnecting first and second implant members, comprising:

a connector body extending generally along a rotational axis and including first and second receiver portions axially offset from one another along said rotational axis and including a threaded portion extending axially from said second receiver portion, said first receiver portion defining a first passage therethrough sized to receive a portion of the first implant member therein, said second receiver portion defining a second passage therethrough sized to receive a portion of the second implant member therein;

a washer member including a first end, an opposite second end, and an axial passage extending therethrough from said first end to said second end, said second receiver portion of said connector body positioned within said axial passage and movably coupled with said washer member to permit rotational movement of said washer member about said rotational axis and translational movement of said washer member along said rotational axis, said washer member including a channel extending transversely therethrough in communication with said axial passage and generally aligned with said second passage of said connector body; and a lock member threadingly engaged with said threaded portion of said connector body, said lock member including an end surface configured to rotate said lock member about said connector body, wherein threading engagement of said lock member along said threaded portion of said connector body exerts an axial force onto the second implant member positioned within said second passage of said connector body to thereby compress the second implant member within said channel in said washer member when said lock member is rotated about said connector body, said axial force displaces said washer member along said rotational axis and into compressed engagement with the first implant member positioned within said first passage of said connector body to thereby lock said washer member and the second implant member at a select angular orientation relative to said connector body, said axial force also compresses the first implant member into clamped engagement against said first receiver portion of said connector body to thereby lock the first implant member within said first passage of said connector body.

2. The connector assembly of claim 1, wherein threading engagement of said lock member along said threaded portion of said connector body is solely responsible for providing said axial force to lock the first and second implant members in position within said first and second passages in said connector body and to lock the first and second implants at a select angular orientation relative to one another.

3. The connector assembly of claim 1, further comprising an annular ring engaged between said lock member and the second implant member positioned within said second passage of said connector body.

4. The connector assembly of claim 1, wherein said first passage in said connector body extends along a first transverse axis, said second passage in said connector body extends along a second transverse axis, said first transverse axis arranged substantially perpendicular to said second transverse axis.

5. The connector assembly of claim 1, wherein said first and second receiver portions and said threaded portion of said connector body are unitarily integral with one another to thereby define a monolithic single-piece structure.

6. The connector assembly of claim 1, wherein said first and second receiver portions of said connector body are rigidly and non-rotatably connected to one another.

7. The connector assembly of claim 1, wherein said channel in said washer member includes a pair of opposing angled side surfaces that are inwardly tapered relative to one another along said rotational axis toward said first end of said washer member, the second implant member engaged with said angled side surfaces to define two points of direct contact between the second implant member and said washer member.

8. The connector assembly of claim 1, wherein said channel in said washer member comprises an elongate slotted opening that opens onto said second end of said washer member and has a length extending toward said first end of said washer member generally along said rotational axis.

9. The connector assembly of claim 1, further comprising a drive member including a distal drive portion having a first series of drive teeth; and
wherein said end surface of said lock member has a second series of drive teeth configured to rotatingly intermesh with said first series of drive teeth defined by said distal drive portion of said drive member; and
wherein said first series of drive teeth is rotatingly intermeshed with said second series of drive teeth whereby rotation of said distal drive portion of said drive member about a drive axis correspondingly rotates said lock member about said rotational axis and threadingly engages said lock member along said threaded portion of said connector body.

10. The connector assembly of claim 9, wherein said threaded portion of said connector body comprises an externally threaded stem and said lock member comprises an internally threaded nut threadingly engaged along said stem.

11. The connector assembly of claim 9, wherein said drive axis is arranged substantially perpendicular to said rotational axis.

12. The connector assembly of claim 9, wherein said second series of drive teeth extend from an axially facing end surface of said lock member in a direction generally along said rotational axis toward said washer member.

13. The connector assembly of claim 12, further comprising a spacer member engaged between said lock member and the second implant member positioned within said second passage of said connector body to maintain a spacing between said second series of drive teeth on said lock member and the second implant member.

14. The connector assembly of claim 13, wherein said spacer member comprises an annular ring engaged within an annular groove in said lock member.

15. The connector assembly of claim 9, wherein said washer member includes at least one aperture extending in a direction substantially perpendicular to said rotational axis, said distal drive portion of said drive member including a stem portion positioned within said aperture in said washer member to maintain intermeshing engagement of said first series of drive teeth with said second series of drive teeth.

16. The connector assembly of claim 15, wherein said washer member includes a flattened region defining a generally planar outer surface with said aperture formed in said generally planar outer surface, said distal drive portion of said drive member including a generally planar end surface positioned in abutment against said generally planar outer surface of said washer member.

17. The connector assembly of claim 1, wherein said washer member comprises a single-piece washer element.

18. The connector assembly of claim 1, further comprising at least one flexible spacer element positioned axially adjacent said first passage in said connector body to provisionally prevent said first end of said washer member from partially covering said first passage; and
wherein said flexible spacer element deforms as said washer member is displaced over said flexible spacer element to allow said compressed engagement of said washer member against the first implant member positioned within said first passage of said connector body.

19. The connector assembly of claim 1, further comprising an implant member and an elongate support member; and
wherein said implant member includes a bone engaging portion and a proximal post portion extending from said bone engaging portion, said proximal post portion positioned within said first passage of said connector body; and
wherein said elongate support member includes a portion positioned within said second passage of said connector body and extending through said channel in said washer member.

20. A connector assembly for interconnecting first and second implant members, comprising:
a connector body extending generally along a rotational axis and including first and second receiver portions axially offset from one another along said rotational axis and including an externally threaded stem portion extending axially from said second receiver portion, said first receiver portion defining a first passage therethrough sized to receive a portion of the first implant member therein, said second receiver portion defining a second passage therethrough sized to receive a portion of the second implant member therein;
a washer member including a first end, an opposite second end, and an axial passage extending therethrough from said first end to said second end, said second receiver portion of said connector body positioned within said axial passage and movably coupled with said washer member to permit rotational movement of said washer member about said rotational axis and translational movement of said washer member along said rotational axis, said washer member including a channel extending transversely therethrough in communication with said axial passage and generally aligned with said second passage of said connector body;

a nut member threadingly engaged with said stem portion of said connector body, said nut member having a first series of drive teeth extending about said rotational axis; and a drive member including a distal drive portion having a second series of drive teeth extending about a drive axis and rotatingly intermeshed with said first series of drive teeth defined by said nut member whereby rotation of said distal drive portion about said drive axis correspondingly rotates said nut member about said rotational axis and threadingly advances said nut member along said stem portion of said connector body, wherein threading advancement of said nut member along said stem portion exerts an axial force onto the second implant member positioned within said second passage of said connector body to thereby compress the second implant member within said channel in said washer member, said axial force displaces said washer member along said rotational axis and into compressed engagement with the first implant member positioned within said first passage of said connector body to thereby lock said washer member and the second implant member at a select angular orientation relative to said connector body, said axial force also compresses the first implant member into clamped engagement against said first receiver portion of said connector body to thereby lock the first implant member within said first passage of said connector body.

21. The connector assembly of claim 20, wherein threading advancement of said nut member along said stem portion of said connector body is solely responsible for providing said axial force to lock the first and second implants in position within said first and second passages in said connector body and to lock the first and second implants at a select angular orientation relative to one another.

22. The connector assembly of claim 20, further comprising a spacer member engaged between said nut member and the second implant member positioned within said second passage of said connector body to maintain a spacing between said first series of drive teeth on said nut member and the second implant member.

23. The connector assembly of claim 20, wherein said first and second receiver portions and said externally threaded stem portion of said connector body are rigidly and non-rotatably connected to one another to thereby define a monolithic single-piece structure.

24. The connector assembly of claim 20, wherein said drive axis is arranged substantially perpendicular to said rotational axis.

25. The connector assembly of claim 20, wherein said first series of drive teeth extend from an axially facing end surface of said nut member in a direction generally along said rotational axis toward said washer member.

26. The connector assembly of claim 20, wherein said washer member includes at least one aperture extending in a direction substantially perpendicular to said rotational axis, said distal drive portion of said drive member including a stem portion positioned within said aperture in said washer member to maintain intermeshing engagement of said first series of drive teeth with said second series of drive teeth.

27. The connector assembly of claim 20, further comprising an implant member and an elongate support member; and wherein said implant member includes a bone engaging portion and a proximal post portion extending from said bone engaging portion, said proximal post portion positioned within said first passage in said connector body; and wherein said elongate support member includes a portion positioned within said second passage in said connector body and extending through said channel in said washer member.

\* \* \* \* \*